(12) United States Patent
Kristiansen et al.

(10) Patent No.: US 8,551,455 B2
(45) Date of Patent: *Oct. 8, 2013

(54) TOOTH CLEANING KIT COMPRISING AT LEAST ONE SET OF CHEWING GUM PIECES

(75) Inventors: Tove Nordestgaard Kristiansen, Jelling (DK); Lars Gyldenvang, Gjerrild Mark (DK); Rikke Mikkelsen, Vejle (DK)

(73) Assignee: Gumlink A/S, Vejle (DK)

( * ) Notice: Subject to any disclaimer, the term of this patent is extended or adjusted under 35 U.S.C. 154(b) by 0 days.

This patent is subject to a terminal disclaimer.

(21) Appl. No.: 11/814,344

(22) PCT Filed: Jan. 27, 2006

(86) PCT No.: PCT/DK2006/000043
§ 371 (c)(1),
(2), (4) Date: Nov. 2, 2007

(87) PCT Pub. No.: WO2006/079342
PCT Pub. Date: Aug. 3, 2006

(65) Prior Publication Data
US 2008/0193506 A1    Aug. 14, 2008

(30) Foreign Application Priority Data
Jan. 28, 2005 (EP) .................................... 05388004
Jan. 28, 2005 (EP) .................................... 05388007

(51) Int. Cl.
*A61Q 11/00* (2006.01)
*A23G 4/06* (2006.01)
*A61K 9/58* (2006.01)

(52) U.S. Cl.
USPC ............................................ 424/48; 424/440

(58) Field of Classification Search
USPC ......................................................... 514/412
See application file for complete search history.

(56) References Cited

U.S. PATENT DOCUMENTS

| | | | |
|---|---|---|---|
| 5,824,291 A | 10/1998 | Howard | |
| 6,235,318 B1 | 5/2001 | Lombardy, Jr. et al. | |
| 2003/0158111 A1* | 8/2003 | Bar-Or | 514/12 |

FOREIGN PATENT DOCUMENTS

| | | |
|---|---|---|
| WO | 94/14424 A1 | 7/1994 |
| WO | 95/25436 A1 | 9/1995 |
| WO | 99/15435 A1 | 4/1999 |
| WO | 00/42861 A1 | 7/2000 |
| WO | 01/14875 A1 | 3/2001 |
| WO | 02/074099 A2 | 9/2002 |
| WO | 03/039503 A1 | 5/2003 |

* cited by examiner

*Primary Examiner* — Frederick Krass
*Assistant Examiner* — Michael P Cohen
(74) *Attorney, Agent, or Firm* — Sughrue Mion, PLLC (57) ABSTRACT

The invention relates to a tooth cleaning kit comprising at least one set of chewing gum pieces for sequentially or simultaneously chewing, wherein the individual set comprises at least one first chewing gum piece having a first formulation and at least one second chewing gum piece having a second formulation, which second formulation is different from said first formulation, and at least one of said first formulation and said second formulation comprises an anti-gingivitis agent.

14 Claims, 1 Drawing Sheet

TOOTH CLEANING KIT COMPRISING AT LEAST ONE SET OF CHEWING GUM PIECES

The present invention relates to a tooth cleaning kit comprising at least one set of chewing gum pieces for simultaneously or sequentially chewing.

Chewing gum with certain specific effects in the mouth is known in general. Such chewing gum is e.g. disclosed in the U.S. Pat. Nos. 5,380,530; 5,693,334; 6,365,130; and US patent publication No. 2004/0115247 A1. These types of chewing gum have only been capable to demonstrate a limited capacity for tooth cleaning for single day use or at the most for use during a few days when a toothbrush is accidentally not available. After such a day a thorough cleaning with toothbrush and toothpaste has been required. Chewing gum of the mentioned type is supplied in a box containing identical pieces of chewing gum.

For several decades professionals and also in general adults and particularly parents have been convinced that the only suitable method of properly cleaning teeth is daily use of a toothbrush and toothpaste. Brushing of teeth with a toothbrush is, however, rather rough on the teeth and especially on the gingiva and will eventually lead to abrasive damage on the treated teeth or on the gingiva.

From time to time most people experience that a toothbrush is unavailable and then have to resort to using other means, such as a chewing gum or lozenge or using mouth wash, in order to at least obtain a sensation of fresh breath. But in doing so they are clearly aware that such use does not account to proper tooth cleaning.

People typically continue to brush teeth daily even when they experience brushing damages or abrasive damages. During a lifetime most people experience to change to use toothbrushes having softer bristles, but these changes occur when a new toothbrush is bought, such as e.g. once a month.

In general, people use the same toothpaste every day throughout the year when brushing teeth. They do not change brushing procedure according to their momentarily need or temporary problems with mouth hygiene.

An object of the present invention is to provide a tooth cleaning kit providing the user with a flexibility to daily adapt the tooth cleaning procedure or procedures to the actual mouth condition.

With a view to this, the present invention relates to a tooth cleaning kit comprising at least one set of chewing gum pieces for sequentially or simultaneously chewing, wherein the individual set comprises at least one first chewing gum piece having a first formulation and at least one second chewing gum piece having a second formulation, which second formulation is different from said first formulation, and at least one of said first formulation and said second formulation comprises an anti-gingivitis agent.

By providing the user with a set of several pieces of tooth cleaning chewing gum pieces of at least two different formulations the user has at every tooth cleaning procedure a choice of using the complete set of the several pieces provided or of using only one or some of the tooth cleaning chewing gum pieces. This is in particular of advantage with respect to gingivitis. Gingivitis is a condition that can come and go over time, and sometimes within days. If a person expects or experiences a condition of gingivitis the tooth cleaning kit can be administered to enhance the effect of said anti-gingivitis agent. On the other hand, when such enhanced effect is not required, the person can from the administering of one set to the next stop chewing one of the formulations containing said anti-gingivitis agent.

It is of course possible according to the present invention that both formulations comprise at least one an anti-gingivitis agent, such as one low dose anti-gingivitis agent in the first formulation and a higher dose anti-gingivitis agent or a plurality of anti-gingivitis agents in the second formulation providing this with an enhanced level of active agents to inhibit or counter gingivitis. The first chewing gum piece can then be of the type "Regular use", and the second chewing gum piece can be of the type "Conditional use". It is also possible according to the present invention that the anti-gingivitis agent is present only in the first formulation, in which case the second formulation can comprise a high level of e.g. anti-plaque agents. In this manner the anti-gingivitis agent is chewed at every cleaning procedure, and when the user senses plaque on the teeth one or more second chewing gum pieces are also chewed.

When the kit for cleaning teeth according to the present invention is embodied for treating a specific tooth or mouth condition of the user, the individual set preferably includes at least one first chewing gum piece for basic teeth cleaning and at least one second chewing gum piece for treatment of a specific teeth condition. It is a distinct advantage that the user can be provided with a kit designed to treat his or hers special problems. If the condition is only slightly pronounced the set can include only a single second chewing gum piece, whereas it can include two or more pieces if the condition is more aggravated. In this manner the dosage of active agents to treat the condition can be obtained by varying the number of used standard chewing gum pieces containing the agent. This provides the manufacturer of the benefit of manufacturing one and the same piece of chewing gum for users requiring different dosages, and the user obtains the benefit of enhanced action of a particular size of dose, because the distribution of the complete dose on several pieces of chewing gum causes the user to chew the gum pieces over an extended period of time, thus prolonging the action of the active agents.

The tooth cleaning kit thus in an easy manner provides the user with the flexibility to adapt the tooth cleaning procedure provided by administering the kit to an actual current condition of the user.

An additional advantage of the tooth cleaning kit is that it presents the user with a substitute for a toothbrush and toothpaste for daily tooth cleaning. By using several pieces of chewing gum having tailored teeth cleaning properties instead of using a toothbrush allows the user to maintain a healthy mouth condition without the highly undesired toothbrush-effect of causing abrasive damage on the teeth and gingiva.

The tooth cleaning kit also provides the user with the flexibility to first have one or more active substances administered to the oral cavity by initially chewing the first piece of chewing gum from the kit for a first period of time and then subsequently chewing the second piece of chewing gum from the kit during a second period of time, thereby administering further active substances to the oral cavity. In this sequential manner it is possible to obtain an improved effect of the active substances.

The kit can also provide the user with the flexibility of simultaneous or part-simultaneous—part-sequential chewing of the first piece of chewing gum from the kit and the second piece or second pieces of chewing gum from the kit, thereby administering active substances to the oral cavity. The first piece of chewing gum may remain in the mouth when the second piece is taken. It is consequently very easy for the user to vary the doses of active ingredients by selecting which chewing gum pieces are chewed from the tooth cleaning kit and by selecting the timing of when and for how long the chewing gum pieces in the kit are chewed.

Said first formulation and said second formulation are different at least in respect of active tooth cleaning agents (substances) included in the formulations. A difference in formulation is not to be taken as a difference in taste ingredients, color or another feature without any influence on the tooth cleaning effect of the chewing gum pieces of the formulation, because such differences would not allow the user to adapt the tooth cleaning procedure to the actual mouth condition. However, a difference in formulation can be a difference in the number and/or in the types and/or in the amounts of active tooth cleaning agents comprised in the formulation. And it can also be a difference in a manner in which an active ingredient is included in the formulation as this manner can influence e.g. the release rate of the agent or the stability of the agent during storage of the kit.

In a preferred embodiment several sets of chewing gum pieces are included in the kit. The embodiment is an alternative to providing just a single set of chewing gum pieces in the kit. When a set comprises only few pieces of chewing gum, such as two or three pieces, the user may find it inconvenient if the complete kit only provides the user with a single set. Preferably, each individual set is provided for one tooth cleaning procedure. In a further development the kit includes several individual sets for use during a single day. By supplying the sets needed for performing several teeth brushing procedures in a single kit the user is given an incentive to use the several sets during one day. This can in particular be an advantage in relation to children or other persons who can have difficulties in keeping track of the number of sets utilized for cleaning teeth during the day. In this respect the user obtains the assistance of having information indicating the number of tooth cleanings performed during the day, information of a kind unavailable when using a toothbrush.

In an embodiment the individual set of the kit comprises several first chewing gum pieces. By having a set with several of said chewing gum pieces the user obtains the possibility of either using the pieces sequentially and thus obtain a more prolonged duration of the action of the agents active for tooth cleaning, or using the pieces concurrently, or partly concurrent partly sequential, in order to both increase the dose level and increase the duration of the impact of the dose.

In order to further improve the flexibility the tooth cleaning kit can in an embodiment have a number of said first chewing gum pieces in the kit that is higher than the number of said second chewing gum pieces in the kit. This allows the user to obtain a particularly long duration or to change the duration of chewing the first gum pieces.

In a preferred embodiment the kit comprises a plurality of sets of chewing gum pieces, which sets are arranged in correspondence with a predetermined period of time, such as one day, one week, or one month. Such a kit includes the sets of chewing gum pieces required for a predetermined long-term procedure of cleaning teeth. In such a kit the sets can be arranged on several individual sheets, such as one sheet with a number of e.g. three sets for use during a single day, and e.g. seven sheets included in the complete kit predetermined to last for one week. This facilitates the use of the kit.

In a preferred embodiment said at least one first chewing gum piece of the first formulation comprises gum base and at least one whitening agent, at least one fresh-breath agent, at least one anti-plaque agent or anti-gingivitis agent, and at least one re-mineralization agent. By using gum base in the pieces of chewing gum it is possible to provide a basis for a dental care product having excellent properties in respect of avoiding abrasive damage on teeth. As gum base alone does not have sufficient cleaning effect to secure an effective daily cleaning of teeth there is added a number of active ingredients to the gum base.

It has been found that regular chewing of first chewing gum pieces formulated with at last one whitening agent, at least one fresh-breath agent, at least one anti-plaque agent or anti-gingivitis agent, and at least one re-mineralization agent can produce a cleaning effect which makes it possible to avoid the use of a toothbrush and yet maintain the teeth and gingiva in well cleaned condition. By dispensing with the use of a toothbrush the user obtains a major benefit in that abrasive damages caused by brushing teeth are avoided. Although it is desirable to embody the tooth cleaning kit to be capable of cleaning teeth with an efficiency that is overall comparable to cleaning teeth with toothbrush and toothpaste, the use of a toothbrush might to some degree be more effective in certain of the desirable effects than the effects of using the present dental care product. This may however be outbalanced by avoiding the undesired effect of abrasive damage on the teeth and gingiva.

Furthermore, it has also appeared that the kit for dental care according to the invention is much easier and more convenient in use than the conventional toothbrush with toothpaste. This is particularly advantageous in case of children and disabled persons to whom handling of a toothbrush can be extremely difficult, which fact may very easily lead to the effect that the teeth cleaning become ineffective.

The availability of the present dental care product is much higher than for a toothbrush, because the gum will normally be carried with or on the user, whereas a toothbrush is kept in the bathroom. The dental care product according to the invention can be used anywhere at any time, as there is no need for access to water, like e.g. in a bathroom. Consequently, the dental care product according to the invention can be used when driving a car, during work, while watching television etc., thereby providing much more freedom to the user.

The individual chewing gum will typically be used for longer duration than the time spent on brushing teeth. When a toothbrush is used the recommended duration of brushing is 2 minutes, but many persons spend less time than that. After completed brushing of teeth it is common to rinse the mouth with water, and in doing so the active substances in the toothpaste are washed out from the mouth. However, when using the chewing gum according to the present invention, chewing is much more prolonged and the mouth is exposed to the active ingredients for longer time during the chewing. In addition the user will typically not rinse the mouth with water after completed chewing, and thus the active ingredients released during chewing will remain in the mouth, especially in the confined areas near the gingival facing towards the chins where the need for a cleaning effect is the most pronounced. It is also a benefit of the present invention that the active ingredients will automatically spread to all surfaces in the mouth, whereas a toothbrush is only really effective in the areas that are actually brushed by the action of the user.

In order to obtain fine tooth cleaning properties of the kit according to the invention it is preferred that at least one of the chewing gum pieces in the set, preferably said at least one first chewing gum piece of the first formulation, includes at least one anti-calculus agent to provide an anti-calculus effect.

In one preferred embodiment said at least one second chewing gum piece of the second formulation comprises gum base and at least one anti-gingivitis agent, preferably a plurality of anti-gingivitis agents. This embodiment provides the user with an effective means for avoiding gingivitis.

In another particularly advantageous embodiment said at least one second chewing gum piece of the second formulation comprises gum base and at least one anti-plaque agent, preferably a plurality of anti-plaque agents. If a person experiences a condition of plaque or wants to prevent such a condition the embodiment allows the person to initiate a temporary use of the second chewing gum piece or pieces which provide an enhanced level of active agents to treat plaque.

In a further embodiment said at least one second chewing gum piece of the second formulation comprises gum base and at least one re-mineralization agent, preferably a plurality of re-mineralization agents. If a person experiences a condition of caries or wants to prevent such a condition the embodiment allows the person to initiate a temporary use of the second chewing gum piece or pieces which provide an enhanced level of active agents causing re-mineralization of the teeth.

In a further embodiment said at least one second chewing gum piece of the second formulation comprises gum base and at least one anti-calculus agent, preferably a plurality of anti-calculus agents. If a person experiences a condition of calculus formation or wants to prevent such a condition the embodiment allows the person to initiate a temporary use of the second chewing gum piece or pieces which provide an enhanced level of active agents against calculus.

In the event a treatment of a specific mouth or tooth condition requires an increase of the dosage or the duration of active agents it is preferred that there are two or more second chewing gum pieces included in the set. If the concentration of the active agent has to be increased the two or more pieces can be chewed together, and in case the duration of the action of the active agent is of importance, then the pieces can be chewed one after the other in order to obtain a prolonged tooth cleaning action.

The kit preferably is for use in the treatment of gingivitis, but it can alternatively or additionally be for use in the treatment of plaque, or another tooth or mouth condition.

In a preferred embodiment of the tooth cleaning kit the at least one first chewing gum piece is for use as basic teeth cleaning and said at least one second chewing gum is for use in the treatment of a specific tooth condition. The user can then use said at least one first chewing gum piece on a regular basis, such as three or four times a day with a chewing time of at least five minutes for the individual chewing gum piece, and said at least one second chewing gum can be used only when it is required due to a specific tooth condition or in order to prevent such a specific condition from developing.

To obtain the effects desired in ordinary tooth cleaning, the chewing gum pieces in the set should include at least one whitening agent, at least one fresh-breath agent, and at least one anti-plaque agent or anti-gingivitis agent or at least one of both of these agents, viz. at least one anti-plaque agent and at least one anti-gingivitis agent. The chewing gum pieces can optionally include at least one re-mineralization agent to obtain better tooth maintenance properties.

The tooth cleaning kit is preferably used as a prophylactic treatment against one or more of the above-mentioned specific tooth conditions. It is thus possible to maintain a completely healthy tooth and mouth condition by using tooth cleaning kits according to the present invention.

An additional advantage of the kit according to the above-mentioned embodiments is the ability to keep some active substances separate from other active substances prior to performing the tooth cleaning because some of the active substances may be included in said first chewing gum piece and other of the active substances may be included in one or more of said second chewing gum pieces. The possibility of keeping active substances strictly apart until use, thereby avoiding break down of substances due to undesired reaction, allows the active substances to be kept potent until use.

It is possible to combine mouth care by tooth brushing with mouth care by chewing of chewing gum pieces of the kit according to the present invention in order to obtain cleaning of teeth in a more gentle way than obtainable by the traditional tooth brushing. In this manner the toothbrush can be slowly phased out as the user gradually recognizes the benefits of cleaning teeth by using kits according to the present invention.

By the term "whitening agents" as used herein is meant any agent, which is able to modify the color of the teeth or to remove or bleach intrinsic or extrinsic stains on or in tooth surfaces for example by oxidizing organic pigments or chromogens in the tooth.

The whitening agents are conveniently selected from teeth color modifying substances that may be considered among the oral care actives useful in the chewing gum according to the invention. These substances are suitable for modifying the color of the teeth in order to satisfy the consumer. Examples of such whitening agents are those listed in the CTFA Cosmetic Ingredient Handbook, 3.sup.rd Edition, Cosmetic and Fragrances Association Inc., Washington D.C. (1982), which are incorporated herein by reference. Specific examples include talc, mica, magnesium carbonate, calcium carbonate, calcium pyrophosphate, baking soda, Icelandic moss, bamboo, sodium hexametaphosphate, magnesium silicate, aluminum magnesium carbonate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. Typical levels are from about 0.05% to about 20%, preferably from about 0.1% to about 15% and most preferably from about 0.25% to about 10%, by weight, of the composition.

Whitening agents for use herein may also comprise materials that remove or bleach intrinsic or extrinsic stains on or in tooth surfaces. Examples of such whitening agents are peroxides, metal chlorites, perborates, percarbonates, peroxyacids, persulphates, and combinations thereof. Suitable peroxide compounds include hydrogen peroxide, urea peroxide, calcium peroxide, carbamide peroxide and mixtures thereof. Suitable metal chlorites include calcium chlorite, barium chlorite, magnesium chlorite, lithium chlorite, sodium chlorite and potassium chlorite. As additional bleaching substances hypochlorite, and chlorine dioxide may be mentioned. A preferred percarbonate is sodium percarbonate. Preferred persulphates are oxones. The content of these substances is dependent on the available oxygen or chlorine. The content of these ingredients in the chewing gum according to the invention is generally in the range from about 0.1% to about 35%, preferably from about 1% to about 25% and most preferably from about 5% to about 10%, by weight of the chewing gum.

In a preferred embodiment the whitening agent is selected from the group consisting of baking soda, Icelandic moss, Icelandic moss extract, bamboo, bamboo extract, calcium pyrophosphate, calcium carbonate, sodium hexa-metaphosphate, nature identical substitutes thereof, and mixtures thereof.

In another embodiment whitening agents are selected from the group consisting of baking soda, Icelandic moss, bamboo, calcium pyrophosphate, calcium carbonate, and sodium hexa-metaphosphate.

In the most preferred embodiment the whitening agent are selected from $NaHCO_3$, calcium carbonat, calcium pyrophosphate, titandioxid, and sodium hexa-metaphosphate.

By the term "fresh-breath agents" as used herein is meant any agent, which is able to control mouth-odor-causing bacteria, as for example agents which are able to control hydrogen sulphide-forming bacteria, as well as any agent which is able to absorb, adsorb, bind or otherwise complex the volatile oral malodour materials.

The fresh-breath agents are preferably selected from agents for oral malodour control, which include a wide variety of materials. Suitable in the chewing gum according to the invention are anti-microbial agents. Such agents may include 5-chloro-2-(2,4-dichlorophenoxy)-phenol, commonly referred to as triclosan, and described in the Merck Index, 11$^{th}$ Edition, (1989), pp 1529 (entry No. 9573) in U.S. Pat. No. 3,506,720, and in European Patent publication No. 0 251 591, phthalic acid and its salts including, but not limited to those disclosed in U.S. Pat. No. 4,994,262, preferably magnesium mono-potassium phthalate, chlorohexidine (Merck Index, No. 2090), alexidine (Merck Index, No. 222), hexetidine (Merck Index, No. 4624), sanguinarine (Merck Index, No. 8320), benzalkonium chloride (Merck Index, No. 1066), salicylanilide (Merck Index, No. 8299), domiphen bromide (Merck Index, No. 3411), cetylpyridinium chloride (CPC) (Merck Index, No. 2024), tetradecylpyridinium chloride (TPC), N-tetradecyl-4-ethylpyridinium chloride (TDEPC), octenifine, delmopinol, octapinol, and other piperidine derivatives, nicin preparations, zinc/stannous ion agents, antibiotics, such as augmentin, amoxicilline, tetracycline, doxycycline, hexadine, minocycline, and metronidazole, and analogues and salts of the above, methyl salicyclate, and mixtures of any of the above.

Illustrative zinc sources in the form of compounds with fresh breath properties for use as fresh-breath agents are zinc oxide, zinc silicate, zinc carbonate, zinc acetate, zinc phosphate, zinc stannate, zinc tetrafluoroborate, zinc hexafluorosilicate, zinc citrate, zinc benzoate, zinc oxalate, zinc stearate, zinc chloride, zinc sulfate, zinc nitrate, zinc phenolsulfonate, zinc carboxymethylsuccinate, and the like. The zinc compounds may also be present as a complex, with a complexing agent such as polyethylenimine or ethylenediamine tetraacetic acid.

A further group of natural extracts which are useful for their oral malodour control benefits include extracts obtained from the tea (green tea, red tea, white tea and black tea), honey suckle, coriander, thyme, propolis, tea tree oil, barberry bark, champex®, sunphenon, applephenon, gold thread, magnolia plants or mixtures thereof. It is preferred that chewing gum according to the present invention comprise from about 0.01% to about 5%.

Extracts suitable for use in the present invention can be obtained from any part of the plant including the leaf, stem, bark, pulp, seed, flesh, juice, root and mixtures thereof. In the context of the present invention the term "extract" is intended to encompass infusions, liquid extracts, liquid concentrates of extracts, fractionated extracts and powdered extracts of the plants/berries/fruits etc. Extracts may be obtained by any conventional technique, such as water extraction, ethanol extraction or methanol extraction where appropriate. It is within the standard procedure of a skilled person to perform an appropriate extraction procedure in order to obtain an extract comprising the beneficial substances extracted from the plants, berries or fruits for use in the present invention.

By the term "nature identical substitute" as used herein is meant any natural or artificial compound or combination of compounds, which has a chemical structure identical to that found in nature. Most often a nature identical substitute is found as the main functional component of an extract or as a mixture of two or more of the main functional components in an extract. By the term "functional component" as used herein is meant the component performing the function of whitening the teeth, when mentioned in connection with whitening agents, or performing the function of providing the fresh-breath, when mentioned in connection with fresh-breath agents, etc. No nature identical substitutes can be found for inorganic compounds. The nature identical substitute may be prepared by use of chemical synthesis, by chemical modification of a compound of natural origin or by use of any enzymatical reaction pathway. The term is well known within the art and, therefore, a skilled person will appreciate whether an agent mentioned may or may not be found as a nature identical substitute.

The following essential oils are also known to have antimicrobial activity and are therefore optionally used in the chewing gum according to the present invention. By the term "essential oil" as used herein is meant any oil that impart the characteristic odors of plants. Oils, which are suitable for use in the present invention, include 2-isopropyl-5-methyl-phenol(thymol), geraniol, carvacrol, hinokitiol, eucalyptol, catechol (particularly 4-allyl catechol), and mixtures thereof.

Another class of oral malodour control agents include absorbents. These are used to absorb, adsorb, bind or otherwise complex the volatile oral malodour materials. Examples of such agents include talc, mushroom extract, zeolite, cyclodextrin, silica shell and mixtures thereof. Such materials are preferably used in a range from about 0.5% to about 10%, preferably from about 1% to about 5%, by weight of the chewing gum.

In a preferred embodiment the fresh-breath agent is selected from the group consisting of a zinc source, coriander, coriander extract, green tea, green tea extract, propolis, propolis extract, tea tree oil, barberry bark, barberry bark extract, hexetidine, champes, sunphenol, applephenol, red tea, red tea extract, white tea extract, thyme extract, and mixtures thereof.

In another embodiment fresh-breath agents are selected from the group consisting of zinc acetate, coriander, green tea, propolis, tea tree oil, barberry bark, hexetidine, champes, sunphenol, applephenol, red tea, green tea extract, white tea and thyme extract.

In the most preferred embodiment the fresh-breath agents are selected from the group consisting of green tea extract, zinc acetate, 2-isopropyl-5-methyl-phenol, and eucalyptus.

Plaque is defined as a bacteria-containing substance that collects on the surfaces of the teeth as well as on other surfaces of the oral cavity. Hence, by the term "anti-plaque agents" as used herein is meant any agent, which is able to prevent or inhibit the formation and accumulation of bacterial deposits on the surfaces of the oral cavity or to degrade or remove existing bacterial deposits on the surfaces of the oral cavity.

Examples of anti-plaque agents include xylitol and other anti-microbial agents. The inhibition effects of the xylitol on oral microbes may have better effect when used in conjunction with an extract since the extract is also acting to disable the microbes. Anti-plaque agents include fluoride ion sources.

Typical examples of active ingredients that are particularly desirable from considerations of anti-plaque effectiveness, safety and formulation include: naficillin, oxacillin, vancomycin, clindamycin, erythromycin, trimethoprim-sulphamethoxazole, rifampin, ciprofloxacin, broad spectrum penicillin, amoxicillin, gentamicin, ceftriazoxone, cefotaxime, chloramphenicol, clavunate, sulbactam, probenecid, doxycycline, spectinomycin, cefixime, penicillin G, minocycline, beta-lactamase inhibitors; meziocillin, piperacillin, aztreonam, norfloxacin, trimethoprim, ceftazidime, dapsone; halogenated diphenyl ethers, e.g. 2',4,4'-trichloro-2-hydroxy-diphenyl ether (Triclosan), 2,2'-dihydroxy-5,5'-dibromo-diphenyl ether; halogenated salicylanilides, e.g. 4',5-dibromosalicylanilide, 3,4',5-trichlorosalicylanilide, 3,4',5-tribromo-salicylanilide, 2,3,3',5-tetrachloro-salicylanilide, 3,3,3',5-tetrachloro-salicylanilide, 3,5-dibromo-3'-trifluoromethyl-salicylanilide, 5-n-octanoyl-3'-trifluoromethyl-salicylanilide, 3,5-dibromo-4'-trifluoromethyl-salicylanilide, 3,5-dibromo-3'-trifluoromethyl-salicylanilide (Flurophene); benzoic esters, e.g. methyl-p-hydroxybenzoic ester, ethyl-p-hydroxybenzoic ester, propyl-p-hydroxybenzoic ester, butyl-p-hydroxybenzoic ester; halogenated carbanilides, e.g. 3,4,4'-trichlorocarbanilide, 3-trifluoromethyl-4,4'-dichlorocarbanilide, or 3,3,4'-trichlorocarbanilide; phenolic compounds (including phenol and its homologs, mono- and poly-alkyl and aromatic halo-phenol and their homologs), e.g. phenol, 2-methyl-phenol, 3-methyl-phenol, 4-methyl-phenol, 4-ethyl-phenol, 2,4-dimethyl-phenol, 2,5-dimethyl-phenol, 3,4-dimethyl-phenol, 2,6-dimethyl-phenol, 4-n-propyl-phenol, 4-n-butyl-phenol, 4-n-amyl-phenol, 4-tert-amyl-phenol, 4-n-hexyl-phenol, 4-n-heptyl-phenol, 2-methoxy-4-(2-propenyl)-phenol (Eugenol), 2-isopropyl-5-methyl-phenol (2-isopropyl-5-methyl-phenol), mono- and poly-alkyl- and aralkyl-halophenols, methyl-p-chlorophenol, ethyl-p-chlorphenol, n-propyl-p-chlorophenol, n-butyl-p-chlorophenol, n-amyl-p-chlorophenol, sec-amyl-p-chlorophenol, n-hexyl-p-chlorophenol, cyclohexyl-p-chlorophenol, n-heptyl-p-chlorophenol, n-octyl-p-chlorophenol, o-chlorophenol, methyl-o-chlorophenol, ethyl-o-chlorophenol, n-propyl-o-chlorophenol, n-butyl-o-chlorophenol, n-amyl-o-chlorophenol, tert-amyl-o-chlorophenol, n-hexyl-o-chlorophenol, n-heptyl-o-chloropenol, p-chlorophenol, o-benzyl-p-chlorophenol, o-benzyl-m-methyl-p-chlorophenol, o-benzyl-m,m-dimethyl-p-chlorophenol, o-phenylethyl-p-chlorophenol, o-phenylethyl-m-methyl-p-chlorophenol, 3-methyl-p-chlorophenol, 3,5-dimethyl-p-chlorophenol, 6-ethyl-3-methyl-p-chlorophenol, 6-n-propyl-3-methyl-p-chlorophenol, 6-iso-propyl-3-methyl-p-chlorophenol, 2-ethyl-3,5-dimethyl-p-chlorophenol, 6-sec-butyl-3-methyl-p-chlorophenol, 2-iso-propyl-3,5-dimethyl-p-chlorophenol, 6-diethylmethyl-3-methyl-p-chlorophenol, 6-iso-propyl-2-ethyl-3-methyl-p-chlorophenol, 2-sec-amyl-3,5-dimethyl-p-chlorophenol, 2-diethylmethyl-3,5-dimethyl-p-chlorophenol, 6-sec-octyl-3-methyl-p-chlorophenol, p-bromophenol, methyl-p-bromophenol, ethyl-p-bromophenol, n-propyl-p-bromophenol, n-butyl-p-bromophenol, n-amyl-p-bromophenol, sec-amyl-p-bromophenol, n-hexyl-p-bromophenol, cyclohexyl-p-bromophenol, o-bromophenol, tert-amyl-o-bromophenol, n-hexyl-o-bromophenol, n-propyl-m,m-dimethyl-o-bromophenol, 2-phenyl-phenol, 4-chloro-2-methyl-phenol, 4-chloro-3-methyl-phenol, 4-chloro-3,5-dimethyl-phenol, 2,4-dichloro-3,5-dimethyl-phenol, 3,4,5,6-tetrabromo-2-methylphenol, 5-methyl-2-pentylphenol, 4-isopropyl-3-methylphenol, 5-chloro-2-hydroxydiphenyl-methane; resorcinol and its derivatives, e.g. resorcinol, methyl-resorcinol, ethyl-resorcinol, n-propyl-resorcinol, n-butyl-resorcinol, n-amyl-resorcinol, n-hexyl-resorcinol, n-heptyl-resorcinol, n-octyl-resorcinol, n-nonyl-resorcinol, phenyl-resorcinol, benzyl-resorcinol, phenylethyl-resorcinol, phenylpropyl-resorcinol, p-chlorobenzyl-resorcinol, 5-chloro-2,4-dihydroxydiphenyl-methane, 4'-chloro-2,4-dihydroxydiphenyl-methane, 5-bromo-2,4-dihydroxydiphenyl-methane, 4''-bromo-2,4-dihydroxydiphenyl-methane; and bisphenolic compounds, e.g. bisphenol A, 2,2'-methylene-bis-(4-chlorophenol), 2,2'-methylene-bis-(3,4,6-trichlorophenol)(hexachlorophene), 2,2'-methylene-bis-(4-chloro-6-bromophenol), bis-(2-hydroxy-3,5-dichlorophenyl)-sulfide, and bis-(2-hydroxy-5-chlorobenzyl)-sulfide.

Illustrative of polyphosphate compounds with plaque-inhibiting properties are dialkali metal and tetraalkali metal pyrophosphate and mixtures thereof in a hydrated or unhydrated form. Illustrative of pyrophosphate salts are $Na_2H_2P_2O_7$, $Na_4P_2O_7$ and $K_4P_2O_7$. Other suitable polyphosphates include hydrated or unhydrated alkali metal tripolyphosphates such as $Na_5P_3O_{10}$ and $K_5P_3O_{10}$.

Plaque buffers such as urea, calcium lactate, calcium glycerophosphate and strontium polyacrylates, ammonium carbonate and vitamins such as Vitamins A, C and E are also included.

Nutraceuticals and nutritional supplements may also be added to chewing gums as active agents against plaque. Among these are herbs and botanicals that include, but are not limited to chamomile, echinacea, Eucalyptus and green tea.

Metal cations can also be used as anti-bacterial and anti-plaque agents. The metal cations are selected from the metals of Group 5 (V, Nb, Ta); Group 6 (Cr, Mo, W); Group 7 (Mn, Tc, Re); Group 8 (Fe, Ru, Os); Group 9 (Co, Rh, Ir); Group 10 (Ni, Pd, Pt); Group 11 (Cu, Ag, Au); Group 12 (Zn, Cd, Hg); Group 14 (Ge, Sn, Pb); Group 16 (Se, Te, PO); and mixtures thereof. Preferably the metal cation is selected from any monovalent or divalent cation selected from the group consisting of zinc, manganese, copper, iron, cobalt, silver, selenium, tin and vanadium; preferably from the group consisting of zinc, manganese, copper, iron, silver, and tin; more preferably from the group consisting of zinc, copper, silver and tin and most preferably from the group consisting of zinc and tin.

Illustrative of zinc compounds with plaque-inhibiting properties are zinc oxide, zinc silicate, zinc acetate, zinc carbonate, zinc phosphate, zinc stannate, zinc tetrafluoroborate, zinc hexafluorosilicate, zinc citrate, zinc benzoate, zinc oxalate, zinc stearate, zinc chloride, zinc sulfate, zinc nitrate, zinc phenolsulfonate, zinc carboxymethylsuccinate, and the like. The zinc compound also can be in the form of a complex, with a complexing reagent such as polyethylenimine or ethylenediamine tetraacetic acid.

A wide variety of metal cation salts are useful in the present invention. These include so called "water-insoluble salts" which have a solubility of less than about 0.5 g per 100 ml at 25° C. and "water soluble salts" which have a solubility of greater than or equal to about 0.5 g per 100 ml at 25° C. It is also possible to use mixtures of these salts. Such mixtures can have several advantages in the compositions of the present invention since they are likely to have different complexing properties with the polyphosphate anions. In addition they have different release rates in the saliva and can therefore act to provide controlled release profiles. Examples of salts that are suitable for use herein include acetate, ammonium sulphate, bromide, chloride, chromate, citrate, dithionate, fluorosilicate, tartrate, fluoride, formate, iodide, nitrate, phenol sulphate, salicyclate, sulphate, gluconate, succinate, glycerophosphate, lactate and mixtures thereof.

In a preferred embodiment the anti-plaque agent is selected from the group consisting of a zinc source, ammonium carbamate, eucalyptus, eucalyptus extract, cranberry, cranberry extract, xylitol, chlorhexidine, seaweed, seaweed extract, epigallocatechin gallate, osteopontin, baking soda, nature identical substitutes thereof, and mixtures thereof.

In another embodiment the anti-plaque agents are selected from the group consisting of zinc acetate, ammonium carbamate, eucalyptus, cranberry, xylitol, chlorhexidine, seaweed, osteopontin and baking soda.

In the most preferred embodiment the anti-plaque agents are selected from the group consisting of aronia, eucalyptus, Immuglobuline-lysozyme, xylitol, green tea extract, and zink acetate.

Gingivitis is defined as an inflammation of the gums surrounding the teeth caused by a build up of plaque or food particles. Hence by the term "anti-gingivitis agents" as used herein is meant any agent, which is able to prevent or inhibit an inflammation of the gums surrounding the teeth caused by a build up of plaque or food particles.

Consequently, anti-gingivitis agents can be anti-inflammatory agents, such as salicylic acid derivatives (e.g. aspirin), paraminophenol derivative (e.g. acetaminophen), indole and indene acetic acids (indomethacin, sulindac and etodalac), heteroaryl acetic acids (tolmetin, diclofenac and ketorolac), aryl propionic acid derivatives (ibuprofen, naproxen, ketoprofen, fenopren, oxaprozine), anthranilic acids (mefenamic acid, meclofenamic acid), enolic acids (piroxicam, tenoxicam, phenylbutazone and oxyphenthatrazone), lactic acid bacteria (LAB), Osteopontin (ONP), IG-Lyt, hexefine, Aloe Vera, chlorhexedine, myrrh, or sage.

Examples of anti-gingivitis agents also include psychotherapeutic agents, such as thorazine, serentil, mellaril, millazine, tindal, permitil, prolixin, trilafon, stelazine, suprazine, taractan, navan, clozaril, haldol, halperon, loxitane, moban, orap, risperdal, alprazolam, chlordiaepoxide, clonezepam, clorezepate, diazepam, halazepam, lorazepam, oxazepam, prazepam, buspirone, elvavil, anafranil, adapin, sinequan, tofranil, surmontil, asendin, norpramin, pertofrane, ludiomil, pamelor, vivactil, prozac, luvox, paxil, zoloft, effexor, welibutrin, serzone, desyrel, nardil, parnate, or eldepryl.

In a preferred embodiment the anti-gingivitis agent is selected from the group consisting of chlorhexidine, myrrh, myrrh extract, neem, neem extract, sage, sage extract, aloe vera, aloe vera extract, hexatidine, osteopontin, quince, quince extract, immuglobuline-lysozyme powder, nature identical substitutes thereof, and mixtures thereof. As an example of an immuglobuline-lysozyme powder, the powder sold under the tradename IG-LY 4023 (obtainable from Pedersen's Laboratorium, Vejle, Denmark) may be mentioned.

In another embodiment the anti-gingivitis agents are agents selected from the group consisting of chlorhexidine, myrrh, neem, sage, aloe vera, hexatidine, osteopontin, quince, and immuglobuline-lysozyme powder (Tradename IG-LY 4023, obtainable from Pedersen's Laboratorium, Vejle, Denmark).

In the most preferred embodiment the anti-gingivitis agents are agents selected from the group consisting of osteopontin and Immuglobuline-lysozyme.

Re-mineralization is defined as the reversal of demineralisation of tooth enamel. Hence, by the term "re-mineralization agents" as used herein is meant any agent, which is able to build up the enamel as well as any agent, which is able to inhibit the demineralization of tooth enamel.

Examples of such re-mineralization agents include pH adjusting agents, which may also be added to make the composition safe for oral tissues. These pH adjusting agents, or buffers, can be any material that is suitable to adjust the pH of the composition. Suitable materials include sodium bicarbonate, sodium phosphate, sodium hydroxide, ammonium hydroxide, potassium hydroxide, sodium stannate, triethanolamine, citric acid, hydrochloric acid, sodium citrate, calcium, fluoride, Phoscal, dicalcium phosphate, Osteopontin (ONP), monosodium phosphate, trisodium phosphate, sodium hydroxide, sodium carbonate, pectin, benzocaine, analgesics, sanguinarine extract, metronidazole, strontium chloride, potassium nitrate, carrageenan, cough and cold remedies, and the like.

In a preferred embodiment the re-mineralization agent is selected from the group consisting of calcium fluoride, osteopontin, a chemical complex between casein phosphoprotein and nanoclusters of amorphous calcium phosphate, nature identical substitutes thereof, and mixtures thereof. In a particular embodiment of the invention the compound sold under the tradename phoscal, which is a chemical complex between casein phosphoprotein and nanoclusters of amorphous calcium phosphate, is selected as the re-mineralization agent.

In another embodiment the re-mineralization agents are selected from the group consisting of calcium, fluoride, osteopontin, and a chemical complex between casein phosphoprotein and nanoclusters of amorphous calcium phosphate (tradename phoscal).

In the most preferred embodiment the re-mineralization agents are selected from the group consisting of sodium fluoride, dicalcium phosphate, and carbamide.

As chewing gum stimulates saliva, and a wide range of active ingredients can be added to the chewing gum according to the invention that promotes re-mineralization or alternatively inhibits demineralization, the re-mineralization effect of the chewing gum exceeds the effect of brushing of teeth.

Calculus may be defined as hardened deposit composed of mineralized plaque and saliva. Hence, by the term "anti-calculus agents" as used herein is meant any agent, which is able to prevent or reduce the formation of hardened deposit composed of mineralized plaque and saliva.

Anti-calculus agents suitable for use in the chewing gum according to the invention include phosphates, pyrophosphates, alkali-metal pyrophosphates, polyphosphates, phosphonates, polyphosphonates and mixtures of any of these. Pyrophosphates are among the best known for use in dental care products. The pyrophosphate salts useful in the present invention include the di-alkali metal pyrophosphate salts, tetra-alkali metal pyrophosphate salts and mixtures of any of these in their unhydrated as well as hydrated forms are the preferred species. Di-sodium di-hydrogen pyrophosphate ($Na_2H_2P_2O_7$), tetra-sodium pyrophosphate ($N_4P_2O_7$), and tetrapotassium pyrophosphate ($K_4P_2O_7$) and mixtures thereof are specific examples.

Additional suitable anti-calculus agents include polyacrylates and other polycarboxylates, such as those disclosed in U.S. Pat. No. 3,429,963, U.S. Pat. No. 4,304,766, and U.S. Pat. No. 4,661,341, polyepoxysuccinates, such as those disclosed in U.S. Pat. No. 4,846,650, ethylenediaminetetraacetic acid as disclosed in British Patent No. 490,384, nitrilotriacetic acid and related compounds as disclosed in U.S. Pat. No. 3,678,154, polyphosphonates as disclosed in U.S. Pat. No. 3,737,533, U.S. Pat. No. 3,988,443, and U.S. Pat. No. 4,877,603.

Suitable anti-calculus agents can e.g. be selected from vitamin C, citric acid, and acetic acid.

Gum base refers in general to any commercially available gum base suitable for production of chewing gum. Such gum bases are well-known and available in the market and normally comprise natural and/or synthetic resins and optionally other ingredients. The gum base may be biodegradable.

Chewing gum is the final product, including gum base, active agents and optionally other ingredients such as taste ingredients and coloring agents. The chewing gum is ready to use by the consumer for cleaning teeth.

Active agent means any ingredient that has a direct effect on conditions of the teeth and the gingival. Some active agents may be active against more than one condition, e.g. function as both anti-plaque agent and anti-calculus agent and they are in the present context listed under both functions.

Typically, the chewing gum comprises a water-soluble bulk portion, a water-insoluble chewable gum base portion and typically water-insoluble flavoring agents. The water-soluble portion dissipates with a portion of the flavoring agent over a period of time during chewing. The gum base portion is retained in the mouth throughout the chew.

The insoluble gum base typically comprises elastomers, resins, fats and oils, waxes, softeners and inorganic fillers. Elastomers may include polyisobutylene, isobutylene-isoprene copolymer and styrene butadiene rubber, as well as natural latexes such as chicle. Resins may include polyvinylacetate and terpene resins. Fats and oils may also be included in the gum base, including tallow, hydrogenated and partially hydrogenated vegetable oils, and cocoa butter. Commonly employed waxes include paraffin, microcrystalline and natural waxes such as beeswax and carnauba.

According to an embodiment of the present invention, the insoluble gum base constitutes between about 5 to about 95 percent by weight of the gum. More preferably the insoluble gum base comprises between 10 and 50 percent by weight of the gum and most preferably about 30 to about 48 percent by weight of the gum.

Particularly interesting elastomeric or resinous polymer compounds which advantageously can be used in a process according to the invention include polymers which, in contrast to currently used elastomers and resins, can be degraded physically, chemically or enzymatically in the environment after use of the chewing gum, thereby giving rise to less environmental pollution than chewing gums based on non-degradable polymers, as the used degradable chewing gum remnants will eventually disintegrate and/or can be removed more readily by physical or chemical means from the site where it has been dumped.

Preferably if degradable, the chewing gum comprises at least two different biodegradable polymers wherein at least one of said bio-degradable polymers comprises a polyester polymer.

One of said at least two different biodegradable polymers may comprise a polyester produced through reaction of at least one alcohol or derivative thereof and at least one acid or derivative thereof. Another of said at least two different biodegradable polymers may comprise a polyester obtained by polymerization of at least one cyclic ester.

The gum base typically also includes a filler component. The filler component may be magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood, and combinations thereof. The filler may constitute between about 5 and about 60 percent by weight of the gum base. Preferably, the filler comprises about 5 to about 50 percent by weight of the gum base.

Gum bases typically also contain softeners, including glycerol monostearate and glycerol triacetate. Furthermore, gum bases may also contain optional ingredients such as antioxidants, colors, and emulsifiers, such as lecithin, sweeteners and flavors. The present invention contemplates employing any commercially acceptable gum base.

The water-soluble portion of the chewing gum may further comprise softeners, sweeteners, flavoring agents and combinations thereof. Softeners are added to the chewing gum in order to optimize the chew ability and mouth feel of the gum. Softeners, also known in the art as plasticizers or plasticizing agents, generally constitute between about 0.1 to about 15.0 percent by weight of the chewing gum. Softeners contemplated by the present invention include glycerine, lecithin, and combinations thereof. Further, aqueous sweetener solutions such as those containing sorbitol, hydrogenated starch hydrolysates, corn syrup and combinations thereof may be used as softeners and binding agents in gum.

The chewing gum pieces can also comprises one or more taste ingredients selected from sweeteners, high-potent sweeteners and flavors. The sweeteners may e.g. be sweeteners like sucrose, dextrose, dextrins, maltose, trehalose, D-tagatose, dried invert sugar, ribose, fructose, levulose, galactose, glucose, maltodextrin, polydextrose, isomalt, sorbitol, sorbitol syrup, mannitol, xylitol, hexa-resorcinol, maltitol, isomaltol, erythriol, lactitol, xylose, tagatose and hydrogenated starch hydrolysates (maltitol syrup). The high potent sweeteners includes the dipeptides aspartame, neotame and alitame; N-sulfonylamides such as saccharin including the salts thereof and acesulfam including the salts thereof; sulfamates such as cyclamate including the salts thereof; chlorinated sugar derivatives such as sucralose; Terpenoid glycosides such as Rebaudioside-A, Stevioside and Glyhyrrhizin; proteins such as thaumatin and monellin and Di-hydrochalcones.

A variety of one or more flavoring agents may be used. Flavoring agents suitable for use in the present invention include natural, natural-identical, and/or artificial flavoring substance, or mixtures thereof, in their solid and/or in their liquid state. The person skilled in the art will recognize that natural and artificial flavoring agents may be combined in any sensorially acceptable blends. Some examples of suitable tastes are peppermint, lemon, and orange.

When taste ingredients like sweeteners and flavors are used, these are normally admixed to the gum base or the active ingredients. Taste ingredients in the chewing gum stimulates the user to chew for a prolonged period of time, which again have the advantages that the active ingredients has a longer period to be released and affect teeth and gingival surfaces.

Consequently, the polishing material can be any material that does not abrade dental enamel and dentine. Typical materials include silica gels and precipitates, aluminas, phosphates, and mixtures thereof. Specific examples include dicalcium orthophosphate dihydrate, calcium pyrophosphate, Bamboo, tricalcium phosphate, hydrated alumina, beta calcium pyrophosphate, calcium carbonate, sodium polymetaphosphate, sodium hexametaphosphate, Calgen, Giltex, Quadrafos, Hagan phosphate, micromet, calcium phosphate dibasic, calcium monohydrogen phosphate, dicalcium orthophosphate secondary calcium phosphate, carbonic acid calcium salt, cacti, calcichew, calcidia, citrical, aragonite, calcite, valerite, aluminum oxide, alumina, silicon dioxide, silica, silicic anhydride, and resinous abrasive materials such as particulate condensation products of urea and formaldehyde and others such as disclosed in U.S. Pat. No. 3,070,510. Mixtures of polishing agents can also be used.

The silica polishing materials generally have an average particle size ranging between about 0.1 to about 30 microns; and preferably from about 5 to about 15 microns. The polishing agent can be precipitated silica or silica gels, such as the silica xerogels described in U.S. Pat. No. 3,538,230 or in U.S. Pat. No. 3,862,307. Preferred are the silica xerogels marketed under the name "Syloid" by the W. R. Grace and Company, Davison Chemical Division. Also preferred are the precipitated silica materials such as those marketed by the J. M. Huber Corporation under the trade name "Zeodent", particularly the silica carrying the designation "Zeodent 119". The types of silica dental polishing agents useful in the chewing gum of the present invention are described in more details in U.S. Pat. No. 4,340,583. The polishing agents in the chewing gum according to the invention is generally present in the range from about 6% to about 70%, preferably from about 10% to about 50%, by weight of the chewing gum.

The ingredients for each type of chewing gum piece in a set are mixed together, such as by initially melting the gum base and feeding it to a running mixer to which ingredients can be fed and mixed. The base may also be melted in the mixer itself. Color or emulsifiers may also be added at this time. A softening agent such as glycerine may also be added at this time, along with syrup and a portion of the bulking agent. Further portions of the bulking agent may then be added to the mixer. A flavoring agent is typically added with the final portion of the bulking agent. Variations of the described procedure can of course be used.

The chewing gum can also be manufactured as compressed chewing gum tablets. In one embodiment the chewing gum tablet is a compressed mixture of gum base and ingredients of active agents, and optionally of other ingredients. Thus, the gum base is present as granules or powder and is mixed with the active agents, which may also be present as granules or powder, and optionally other ingredients like taste ingredients can also be added to the mixture. Taste ingredients are in a preferred embodiment selected from the group consisting of sweeteners, high-potent sweeteners and flavors. The mixture is filled into a press that presses the mixture to form compressed chewing gum tablets. Use of granules is in particular an advantage when one or more of the active ingredients are sensitive towards elevated temperatures as the mixing and pressing can be done at low temperature, e.g. normal room temperature.

The chewing gum can also be manufactured from traditional coherent gum. In this manner the active agents and optionally other ingredients are mixed into the gum base mass. The mixing operation may take place at elevated temperature to decrease the viscosity of the chewing gum formulation thereby facilitating the mixing. After the mixing the chewing gum formulation is normally sent through rollers to form sheets of chewing gum from which pieces of chewing gum are punched or scored out.

In general, traditional coherent chewing gum is manufactured by sequentially adding the various chewing gum ingredients to a commercially available mixer known in the art. After the ingredients have been thoroughly mixed, the gum mass is discharged from the mixer and shaped into the desired form such as by rolling into sheets and cutting into sticks, extruding into chunks or casting into pellets. Alternatively, coherent chewing gum may be manufactured by extrusion.

It will be recognized to those skilled in the art, that variations of the above-described procedure may be used.

In another embodiment directed at the manufacture of chewing gum tablets of a compressed mixture or blend of materials, gum base granules are included in said mixture before the mixture is pressed into tablets. In a further embodiment ingredients of active agents are present in said gum base granules. These ingredients can be added to the gum base material during the preparation thereof.

Not all active agents need to be added to the gum base material. Preferably, temperature sensitive agents are added to the mixture of gum base granules or gum base powder just before the materials are blended or mixed for conveyance to a tablet pressing apparatus.

At least one fraction of said active agents may be present only in some of said gum base granules, and at least another fraction of said active agents is present only in others of said gum base granules. By making several types of gum base granules containing their respective active agents it is possible to effectively keeping the respective active agents apart, because the final blending or mixing of materials before pressing the tablets does not cause the materials to be actually intermixed into a homogenous mass, but instead the blend or mixture remains a blend or mix of powder, granules etc.

In a further embodiment the ingredients of active agents present in said mixture in one or both of the following forms: granules and powder. And in another embodiment gum base powder is included in said mixture. In addition or as an alternative chewing gum powder can be included in said mixture. This can be of advantage, e.g. if the gum base and other ingredients have been mixed together into a chewing gum mass which is then brought into powder form, such as by freezing and milling. Furthermore, chewing gum granules can be included in said mixture, and also in this embodiment it is possible to include ingredients of active agents in said chewing gum granules; and in a further development at least one fraction of said active agents is present only in some of said chewing gum granules, and at least another fraction of said active agents is pre-sent only in others of said chewing gum granules.

In an embodiment a fraction of said ingredients of active agents is included in said gum base. This can be an advantage, e.g. to control the release rate of the active agents, or to obtain a desirable separation of different active agents in a compressed chewing gum tablet until chewing of the gum. Some agents, like zinc sources and osteopontin, can interact in undesired manners, and this can be avoided by intermixing the one agent into the gum base material, which is formed to gum base granules or chewing gum powder, and by adding powder or granules of the other agent together with additional agents and possible taste ingredients to the blend prepared just before the tablets are pressed. The blend can be a blend of powders, a blend of granules or a blend of powders and granules. The blend is compressed into tablets.

In one embodiment the fraction of said ingredients of active agents can be present in the gum base during mixing thereof prior to shaping the gum base material into gum base granules. During this mixing the temperature is elevated, so the most temperature sensitive agents are preferably added to the blend prepared after the gum base has been shaped into granules or powder.

The fraction of agents intermixed into the gum base can amounts to at least 20% by weight of the total contents of active agents in the chewing gum tablet, and even higher values, such as amounts of at least 30% or at least 40% are also possible.

It is preferred that the first chewing gum piece and/or the second chewing gum piece is chewed for about 5 to about 20 minutes, such as longer than 10 minutes. Chewing for more than 5 minutes allows active ingredients in the chewing gum to be released and be given time to affect the teeth and gingiva. The break down of plaque, calculus, etc. by active ingredients is based on chemical reactions rather than on a mechanical rubbing effect and the longer duration causes improved effects. The first chewing gum piece and/or the second chewing gum piece can be formulated to release the active agents at a rate adapted to the intended chewing time. At the end of the intended chewing time it is preferred that at least 60%, such as at least 80%, of the active agents in the chewing gum piece have been released.

With respect to the first chewing gum pieces and the second chewing gum pieces it is preferred that the anti-gingivitis agent(s) constitute(s) 0.01-20%, such as 0.03-12% of the chewing gum. Preferably the content of anti-gingivitis agent(s) is higher when the anti-gingivitis agent(s) are comprised in the second chewing gum pieces than when comprised in the first chewing gum pieces. The content of the anti-gingivitis agents can be in range of 0.04-10%, such as from 1-8% of the chewing gum.

When present, anti-plaque agent(s) may in an embodiment constitute 0.01-70% of the chewing gum (a high content of anti-plaque agent is in particular desirable when the anti-plaque agent is xylitol), such as 0.03-50%, or 0.05-35% of the chewing gum. Anti-plaque agent(s) can also constitute 1-20%, such as 1.1-15% of the chewing gum. Preferably the content of anti-plaque agent(s) is higher when the anti-plaque agent(s) are comprised in the second chewing gum pieces than when comprised in the first chewing gum pieces.

When present, anti-calculus agent(s) may in an embodiment constitute 0.01-20%, such as 0.03-15% of the chewing gum. Anti-calculus agent(s) can also constitute 0.1-10%, such as 0.4-8% of the chewing gum. Preferably the content of anti-calculus agent(s) is higher when the anti-calculus agent(s) are comprised in the second chewing gum pieces than when comprised in the first chewing gum pieces.

When present, re-mineralization agent(s) may in an embodiment constitute 0.01-20%, more preferred 0.02-10 of the chewing gum. can also constitute 0.1-10%, such as 0.4-8% of the chewing gum. Preferably the content of re-mineralization agent(s) is higher when the re-mineralization agent(s) are comprised in the second chewing gum pieces than when comprised in the first chewing gum pieces.

When present, whitening agent(s) may in an embodiment constitute 0.01-20%, such as 0.03-12% of the chewing gum. Whitening agent(s) can also constitute 0.1-10%, such as 1-9% of the chewing gum. Preferably the content of whitening agent(s) agent(s) is higher when the whitening agent(s) agent(s) are comprised in the second chewing gum pieces than when comprised in the first chewing gum pieces.

When present, fresh-breath agent(s) may in an embodiment constitute 0.01-20%, such as 0.02-8% of the chewing gum. Fresh-breath agent(s) can also constitute 0.1-17%, such as 2-14% of the chewing gum. Preferably the content of fresh-breath agent(s) is higher when the fresh-breath agent(s) are comprised in the second chewing gum pieces than when comprised in the first chewing gum pieces.

In other embodiments the chewing gum according to the invention can be centre filled gum (centre filled with liquid, gel or powder), coated gum or gum formed as sticks. Preferably the gum has an average weight of about 0.5 to 5 g, preferably from 1.5 to 3.5 g.

The set of chewing gum pieces can e.g. be packed in blister packing, and several sets can be blister packed on an insert or a sheet, e.g. with each set occupying a row on said sheet.

The different chewing gum pieces in a set can have coloring enabling the user to differentiate between the individual pieces of gum in a set. When the set includes a first chewing gum piece for basic teeth cleaning and a second chewing gum piece for treatment of a specific teeth condition, said first chewing gum piece can have a color distinctly different from the color of said second chewing gum piece. The kit can in this case be provided as a container with loose chewing gum pieces, and the user then picks a set of chewing gum pieces by taking e.g. one blue piece of gum and one yellow piece of gum.

Differentiation between the pieces of gum in a set can also be provided in other manners, such as by manufacturing the gum pieces in different shapes, or with markers. As an example of this a first chewing gum piece can be conventionally manufactured chewing gum, which has e.g. been scored out of a sheet of chewing gum, and a second chewing gum piece can be a chewing gum tablet of compressed particulate materials. As another example the first and second chewing gum pieces can both be chewing gum tablets, but having different diameters or different heights.

It can be a desire that the chewing gum pieces in a set are taken in a specific sequence. One chewing gum piece can e.g. include an active agent which by acting on the teeth for the some time enhance the effects of a second active agent provided in another piece of chewing gum. When such a sequential chewing of different pieces in a certain order is desired, the different chewing gum pieces in a set is preferably given a shape or color which to the user indicates the correct sequence. As one example of this, a first chewing gum piece can be a chewing gum tablet having only a single layer (or a non-layered tablet), a second chewing gum piece can be a chewing gum tablet having two layers, and if needed a third chewing gum piece can be a chewing gum tablet having three layers etc.

Instead of layers, a user can be provided with similar information on the correct sequence by first pieces having only one color, second pieces having two colors, and if needed a third piece having three colors etc.

A user can be alternatively be provided with similar information on the correct sequence by first pieces having only one marker, second pieces having two markers, and if needed a third piece having three markers etc. The markers can be embossed or stamped onto or into the surface of the chewing gum pieces so that the markers on the chewing gum pieces are presented to the user as markers projecting from the surface of the piece or markers recessed into the surface of the piece. The markers can have any shape or pattern considered expedient to inform the user of the suitable sequence of chewing the pieces in the set, such as actual numbers, such as 1 on the first piece, 2 on the second piece, and if required 3 on the third piece etc. The first piece can also be provided with a marker in form of one dot or slash or line, the second piece with a marker in form of two dots or two slashes or two lines etc.

A user can alternatively be provided with similar information on the correct sequence by first pieces having only one color, second pieces having two colors, and if needed a third piece having three colors.

The pieces in a set can also be distinguished by being provided with printing onto the outer surface of the chewing gum pieces. The printing can be a numbering as just described in connection with markers, or it can be letters or text indicating to the user how the individual chewing gum piece is intended to be used in order to obtain the desired tooth cleaning effect. To give some examples, the set of chewing gum pieces can in one embodiment be composed so that the user has to take one piece of chewing gum for obtaining a normal tooth cleaning and pieces of chewing gum intended for this can be marked with the letter N (or a letter indicating "normal" in another language than English—and correspondingly for other letters) or the letter D for daily, or D1, D2, D3 if the user needs help for performing tooth cleaning three times daily. And in case the user needs tooth cleaning directed at special effects or a current condition related to the users teeth or gingiva the chewing gum pieces made for such a specific task can carry a special marking or special printing, such a M if it is for use once every Monday, G if it contains high doses of anti-gingivitis agents, P if it contains high doses of anti-plaque agents, etc.

The invention will now be further explained with reference to examples and to the schematical drawing on which

All percentages (%) are weight percentages unless otherwise stated.

The chewing gum according to the invention can be conventional chewing gum pieces, compressed chewing gum tablets, sticks, centre-filled chewing gum with the centre filled with liquid, gel or powder. Moreover, the active ingredients, flavor and sweetener may be encapsulated to avoid undesired reactions during storage.

Figure 1:
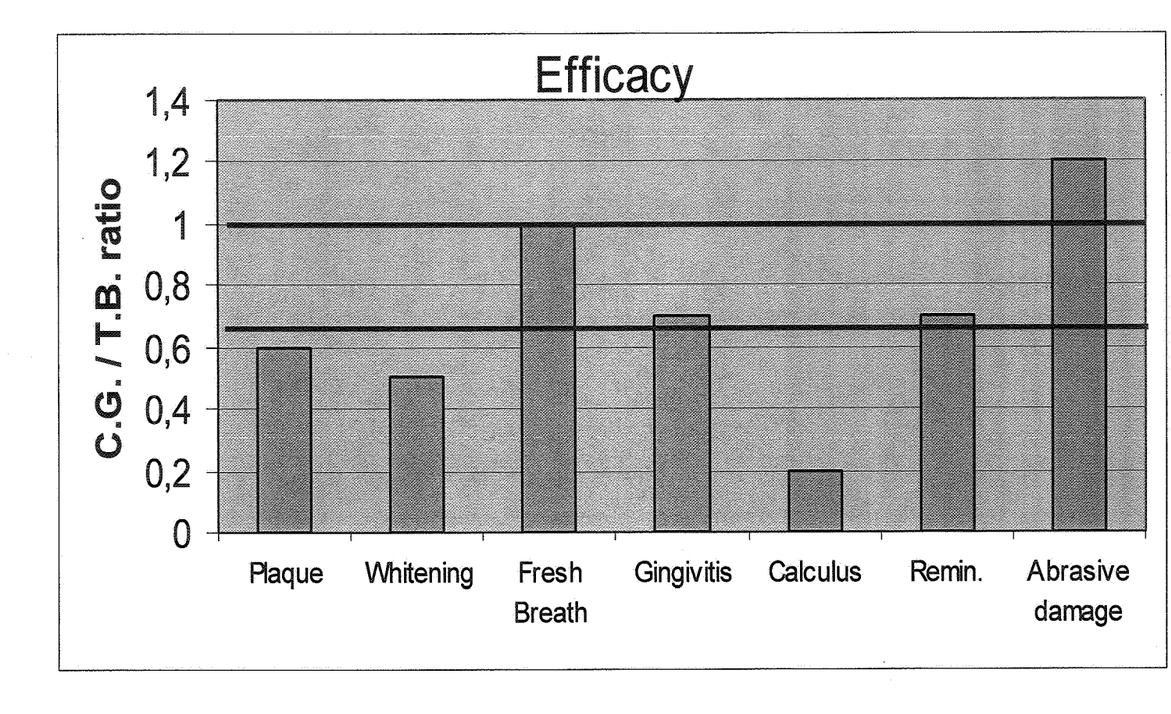
FIG. 1 illustrates an estimate of the efficacy of the chewing gums tested (C.G) (chewing for 5 to 20 minutes) for dental care purposes compared with tooth brushing (T.B) (new toothbrush and correct tooth brushing for 2 minutes).

In FIG. 1 the line 1 indicates the efficacy of a toothbrush and the columns indicates the efficacy of chewing gum in respect of plaque, whitening, fresh breath, gingivitis, calculus, re-mineralization and abrasive damage, respectively. As indicated by the line, the overall efficacy of tested chewing gum compared to tooth brushing is about 67%. The individual effects can be improved by adding more active ingredients and/or by combining ingredients so that the efficacy is raised above 70%, such as an efficacy that exceeds 100% or better efficacy than tooth brushing.

In respect of plaque (efficacy approx 60% for the tested chewing gum) the removal of plaque and/or inhibition of plaque formation can been improved, e.g. by adding zinc acetate to the chewing gum, which will enhance the effect to be close to or better than the efficacy for brushing teeth. In addition, the chewing gum according to the invention will be better than brushing teeth in real life due to the fact that the effect from chewing gum reaches places the toothbrush cannot reach. An in vivo plaque study performed by the inventors shows that e.g. zinc acetate worked in the "hard-to-reach" places with high efficiency.

Moreover, a clinical test has demonstrated that chewing gum with calcium pyrophosphate clinically whitens teeth. Presently, the effect almost matches the effect of a toothbrush with toothpaste. However, by using other agents the whitening effect reaches 100% as compared with tooth brushing.

The fresh breath effect is already better than if brushing teeth, as the chewing gum according to the invention has a much longer contact time with the volatile sulphur compounds to be eliminated. Correct tooth brushing last 2 minutes whereas chewing of chewing gum typically last for at least 5 minutes.

With respect of the anti-gingivitis effect, the chewing gum according to the invention already match this effect compared to brushing of teeth, as the contact time is longer as with brushing teeth, thereby allowing the active substances longer time to affect the infected gingiva.

As chewing gum stimulates saliva, and a wide range of active ingredients can be added to the different chewing gum pieces in the kit according to the invention that promotes re-mineralization or alternatively inhibits demineralization, the re-mineralization effect of the chewing gum exceeds the effect of brushing of teeth.

The toothbrush abrasive effect is in the present context understood as the brushing effect causing abrasive damage on gingiva and the teeth side surfaces. The mechanism involved in development of these damages is understood in the following manner. During the brushing of teeth with a toothbrush, the toothbrush bristles push against the gingiva and cause exposure of the innermost portion of the tooth side surface. This portion of the tooth side surface normally lies well protected behind gingival tissue. This portion is weak in a mechanical sense because the enamel is thin or even missing in this portion. By the brushing the toothbrush bristles act abrading on this weak portion of the tooth side surface. The bristles also penetrate in between the gingiva and said weak portion of the tooth and can cause abrasive damage on the gingival tissue so that gingiva over time is worn down with the result that said weak portion is permanently exposed. With respect to the outer portion of the tooth the enamel is here so thick and strong that the toothbrush cannot in the outer portion really act with an abrasive effect in the sense of the present description. The chewing gum pieces in the kit according to the present invention substantially has no abrasive effect on the soft portions of the teeth and this parameter is naturally dramatically better than brushing teeth.

In the following description examples are given of formulation of chewing gum pieces to be comprised in the tooth cleaning kit according to the invention. The kit has a number of sets, and the individual set has at least one first chewing gum piece, the first chewing gum pieces being exemplified as chewing gum piece 1, and at least one second chewing gum piece, the second chewing gum pieces being exemplified as chewing gum piece 2. A minimum kit thus includes a single set of one chewing gum piece 1 and one chewing gum piece 2. Each single set can include several pieces of chewing gum piece 1 and/or several pieces of chewing gum piece 2. When the kit includes a plurality of sets, the individual sets in the kit need not all have the same number of chewing gum pieces and need not all have chewing gum pieces 1 of identical formulation or chewing gum pieces 2 of identical formulation. When the set includes the chewing gum pieces required for the tooth cleaning procedures for a complete single day, and the kit includes seven sets—covering a week—then the sets for e.g. Saturday and Sunday can have a composition of pieces different from the sets for e.g. Monday to Friday.

EXAMPLE

The chewing gum pieces in the following example were manufactured from a commercially available gum base (Danfree, available from Gumlink A/S, Vejle, Denmark) mixed with sweeteners, taste ingredients and active ingredients. Two different pieces of chewing gum were manufactured with ingredients in the following ratios:

| Chewing gum piece 1: | |
|---|---|
| Gum base | 60.00% |
| Sorbitol | 18.20% |
| Peppermint powder | 1.50% |
| Menthol powder | 0.30% |
| Dicalcium phosphate | 2.70% |
| Green tea | 5.00% |
| Baking soda | 0.40% |
| Calcium carbonate | 4.10% |
| Calcium pyrophosphate | 6.50% |
| Succralose | 0.25% |
| Magnesium stearate | 0.50% |
| *Eucalyptus* powder | 0.50% |

| Chewing gum piece 2: | |
|---|---|
| Gum base | 30.00% |
| Xylitol | 68.80% |
| Peppermint powder | 0.50% |
| Menthole powder | 0.20% |
| Magnesium stearate | 0.50% |

The gum base was granulated (GALA underwater pelletizer) to form granules with diameters in the range of approximately 0.5-1.5 mm and mixed with the active ingredients.

The particulate mixture of formulation 1 (1.5 g) was filled into a tablet pressing machine and compressed to form a first layer. Then 0.7 g pure gum base granules were filled into the tablet pressing machine and compressed onto the first layer to form a barrier layer. Finally 2 g of formulation 2 particulate material was filed into the tablet pressing machine and compressed.

The resulting cylindrical shaped layered chewing gum tablets had an average weight of about 4.2 g and a diameter of about 8 mm.

The chewing gum was evaluated for inhibition of plaque formation in a clinical study.

The test subjects abstained from all oral hygiene for 2 days and either chewed the gum five times per day or used no gum (Plaque scores were assigned using the Modified Quickly-Hein (MQH) index). The result demonstrated that chewing gum comprising xylitol was significantly more effective in inhibiting the formation of plaque on teeth when used as the only means of oral hygiene for two days. Additionally, it was most efficient in areas that are often missed during tooth brushing.

In conclusion, the results demonstrate that the chewing gum containing xylitol is able to reduce dental plaque formation. Moreover, the chewing gum has an ability to make dental plaque less adhesive and thus easier to remove during chewing. As a further benefit, xylitol inhibit bacterial growth and thereby inhibit tooth decay.

The chewing gum was also evaluated for its whitening effect. The chewing gum comprising calcium pyrophosphate not only results in whiter teeth by stain removal, it also helps to prevent further stain after consumption of foods and beverages.

Clinical studies on the inhibition of stain over a 14 days period showed that when chewing, chewing gum according to the invention 20 minutes each day, compared to chewing, chewing gum with 4.5% calcium carbonate, commercially available on the market, the inhibition of stain was considerably improved.

The dicalcium phosphate in the chewing gum improves the re-mineralization rate of the teeth.

Green tea provided excellent fresh breath properties in the chewing gum.

In the following other formulations of chewing gum are described. These formulations are also considered to be useful according to the present invention.

The first 16 formulations are for chewing gum piece 1 of a set and intended for daily oral care and teeth cleaning.

The following formulations are for chewing gum piece 2 for specific purpose.

| Chewing gum piece 1 Formulation example 2 | |
|---|---|
| Ingredients | % by weight |
| Gum base | 39.5 |
| Sorbitol | 39.99 |
| Glycerine | 5 |
| Green tea | 4 |
| Flavour | 2.7 |
| Craneberry | 2.7 |
| Dicalcium phosphate | 2.5 |
| Talc | 2.5 |
| Lecithine | 0.2 |
| Zinc acetate | 0.5 |
| Acesulfane K | 0.2 |
| Aspartame | 0.2 |
| *Aloe vera* | 0.01 |

| Chewing gum piece 1 Formulation example 3 | |
|---|---|
| Ingredients | % by weight |
| Gum base | 50 |
| Sorbitol | 34.98 |
| Flavour | 3 |
| Calcium carbonate | 4 |
| *Eucalyptus* | 3 |
| Xylitol | 4.6 |
| Acesulfane K | 0.2 |
| Aspartame | 0.2 |
| *Aloe vera* | 0.01 |
| Dicalcium phosphate | 0.01 |

| Chewing gum piece 1 Formulation example 4 | |
|---|---|
| Ingredients | % by weight |
| Gum base | 45 |
| Sorbitol | 29.99 |
| xylitol | 10 |
| Maltitol syrup | 5 |
| Glycerin | 2 |
| Flavour | 2 |
| *Aloe vera* | 1.5 |
| Baking soda | 1.5 |
| Champex | 1.5 |
| Black seaweed | 0.9 |
| Acesulfane K | 0.3 |
| Aspartame | 0.3 |
| Dicalcium phosphate | 0.01 |

| Chewing gum piece 1 Formulation example 5 | |
|---|---|
| Ingredients | % by weight |
| Gum base | 39.5 |
| Sorbitol | 39.98 |
| Glycerine | 5 |
| Green tea extract | 3.9 |
| Flavour | 2.5 |
| Grape seed | 3 |
| Calcium carbonate | 3.5 |
| Talc | 1.5 |
| Lecithine | 0.2 |
| Zinc acetate | 0.5 |
| Acesulfane K | 0.2 |
| Aspartame | 0.2 |
| Dicalcium phosphate | 0.01 |
| *Aloe vera* | 0.01 |

| Chewing gum piece 1 Formulation example 6 | |
|---|---|
| Ingredients | % by weight |
| Gum base | 40 |
| Sorbitol | 30.31 |
| Maltitol syrup | 5 |
| Lecithine | 0.2 |
| Green tea extrakt | 1.5 |
| *Aronia* | 2 |
| Zink acetate | 0.06 |

Chewing gum piece 1
Formulation example 6

| Ingredients | % by weight |
| --- | --- |
| Sodium fluoride | 0.03 |
| NaHCO$_3$ | 1 |
| Calcium carbonate | 3 |
| Dicalcium phosphate | 3 |
| Calcium pyrophosphate | 6.7 |
| Titandioxid | 1 |
| Thyme | 0.5 |
| Acesulfame | 0.2 |
| Aspartame | 0.2 |
| Flavour | 1.3 |
| *Eucalyptus* | 1 |
| Xylitol | 5 |

Chewing gum piece 1
Formulation example 7

| Ingredients | % by weight |
| --- | --- |
| Gum base | 40 |
| Sorbitol | 42.07 |
| Maltitol syrup | 5 |
| Lecithine | 0.2 |
| Calcium carbonate | 4 |
| Sodium fluoride | 0.03 |
| *Aronia* | 3 |
| Green tea extrakt | 3 |
| Osteopontin | 0.5 |
| Vitamin C | 0.5 |
| Acesulfame | 0.2 |
| Aspartame | 0.2 |
| Flavour | 1.3 |

Chewing gum piece 1
Formulation example 8

| Ingredients | % by weight |
| --- | --- |
| Gum base | 40 |
| Sorbitol | 44.37 |
| Maltitol syrup | 5 |
| Lecithine | 0.2 |
| NaHCO$_3$ | 1 |
| Sodium fluoride | 0.03 |
| *Aronia* | 3 |
| Green tea extrakt | 3 |
| Osteopontin | 0.5 |
| Vitamin C | 0.5 |
| Acesulfame | 0.2 |
| Aspartame | 0.2 |
| Flavour | 2 |

Chewing gum piece 1
Formulation example 9

| Ingredients | % by weight |
| --- | --- |
| Gum base | 40 |
| Sorbitol | 37.17 |
| Maltitol syrup | 5 |
| Lecithine | 0.2 |
| Calcium pyrophosphate | 7 |
| Sodium fluoride | 0.03 |
| *Aronia* | 3 |
| Green tea extrakt | 3 |
| Osteopontin | 0.5 |
| Vitamin C | 0.5 |
| Acesulfame | 0.3 |
| Aspartame | 0.3 |
| Flavour | 3 |

Chewing gum piece 1
Formulation example 10

| Ingredients | % by weight |
| --- | --- |
| Gum base | 40 |
| Sorbitol | 33.97 |
| Maltitol syrup | 5 |
| Calcium carbonate | 3 |
| Calcium pyrophosphate | 7 |
| Sodium fluoride | 0.03 |
| *Aronia* | 3 |
| Green tea extrakt | 3 |
| Osteopontin | 0.5 |
| Vitamin C | 0.5 |
| NaHCO$_3$ | 1 |
| Acesulfame | 0.25 |
| Aspartame | 0.25 |
| Flavour | 2.5 |

Chewing gum piece 1
Formulation example 11

| Ingredients | % by weight |
| --- | --- |
| Gum base | 40 |
| Sorbitol | 38.9 |
| Maltitol syrup | 5 |
| Lecithine | 0.2 |
| Calcium carbonate | 4 |
| Dicalcium phosphate | 2.5 |
| Acesulfame | 0.2 |
| Aspartame | 0.2 |
| Flavour | 2 |
| *Aronia* | 3 |
| Green tea extrakt | 3 |
| Osteopontin | 0.5 |
| Vitamin C | 0.5 |

Chewing gum piece 1
Formulation example 12

| Ingredients | % by weight |
| --- | --- |
| Gum base | 40 |
| Sorbitol | 37.17 |
| Maltitol syrup | 5 |
| Lecithine | 0.2 |
| Calcium carbonate | 4 |
| Dicalcium phosphate | 2.5 |
| Acesulfame | 0.3 |
| Aspartame | 0.3 |
| Flavour | 3.5 |
| *Aronia* | 3 |

Chewing gum piece 1
Formulation example 12

| Ingredients | % by weight |
|---|---|
| Green tea extrakt | 3 |
| Osteopontin | 0.5 |
| Vitamin C | 0.5 |
| Sodium fluoride | 0.03 |

Chewing gum piece 1
Formulation example 13

| Ingredients | % by weight |
|---|---|
| Gum base | 40 |
| Sorbitol | 33.37 |
| Maltitol syrup | 5 |
| Lecithine | 0.2 |
| Acesulfame | 0.2 |
| Aspartame | 0.2 |
| Flavour | 2 |
| Green tea extrakt | 3 |
| Dicalcium phosphate | 2.5 |
| *Aronia* | 3 |
| Xylitol | 5 |
| Immuglobuline-lysozyme | 5 |
| Vitamin C | 0.5 |
| Sodium fluoride | 0.03 |

Chewing gum piece 1
Formulation example 14

| Ingredients | % by weight |
|---|---|
| Gum base | 45 |
| Sorbitol | 41.17 |
| Maltitol syrup | 5 |
| Acesulfame | 0.3 |
| Aspartame | 0.3 |
| Flavour | 4 |
| Lecithine | 0.2 |
| NaHCO$_3$ | 1 |
| Sodium fluoride | 0.03 |
| Green tea extrakt | 2 |
| Osteopontin | 0.5 |
| Vitamin C | 0.5 |

Chewing gum piece 1
Formulation example 15

| Ingredients | % by weight |
|---|---|
| Gum base | 45 |
| Sorbitol | 41.67 |
| Maltitol syrup | 5 |
| Lecithine | 0.2 |
| *Eucaluptus* | 1.5 |
| NaHCO$_3$ | 0.03 |
| Zinc carbamate | 0.5 |
| Dicalcium phosphate | 3 |
| Osteopontin | 0.5 |
| Acesulfame | 0.2 |
| Aspartame | 0.2 |
| Flavour | 2.2 |

Chewing gum piece 1
Formulation example 16

| Ingredients | % by weight |
|---|---|
| Gum base | 45 |
| Sorbitol | 32.57 |
| Maltitol syrup | 5 |
| Lecithine | 0.2 |
| *Eucaluptus* | 1.5 |
| NaHCO$_3$ | 0.03 |
| Zinc benzoate | 0.5 |
| Dicalcium phosphate | 3 |
| Osteopontin | 0.5 |
| Acesulfame | 0.3 |
| Aspartame | 0.3 |
| Flavour | 2.6 |
| Green te extract | 2 |
| Thymol | 0.5 |
| Xylitol | 4 |
| *Aronia* | 2 |

Chewing gum piece 2 (whitening)
Formulation example 2

| Ingredients | % by weight |
|---|---|
| Gum base | 52 |
| Sorbitol | 31.8 |
| Maltitol syrup | 5 |
| Lecithine | 0.2 |
| *Eucaluptus* | 1.2 |
| NaHCO$_3$ | 3.5 |
| Calcium carbonate | 2.7 |
| Titaniumdioxid | 1.6 |
| Acesulfame | 0.3 |
| Aspartame | 0.3 |
| Flavour | 1.4 |

Chewing gum piece 2 (re-mineralisation)
Formulation example 3

| Ingredients | % by weight |
|---|---|
| Gum base | 45 |
| Sorbitol | 40.69 |
| Maltitol syrup | 5 |
| Lecithine | 0.2 |
| *Eucaluptus* | 1.5 |
| Sodium fluoride | 0.31 |
| Dicalcium phosphate | 4.2 |
| Osteopontin | 0.5 |
| Acesulfame | 0.2 |
| Aspartame | 0.2 |
| Flavour | 2.2 |

Chewing gum piece 2 (plaque)
Formulation example 4

| Ingredients | % by weight |
|---|---|
| Gum base | 45 |
| Sorbitol | 26.57 |
| Maltitol syrup | 5 |
| Lecithine | 0.2 |
| *Eucaluptus* | 1.5 |
| NaHCO$_3$ | 0.03 |

-continued

Chewing gum piece 2 (plaque)
Formulation example 4

| Ingredients | % by weight |
|---|---|
| Zinc benzoate | 1.5 |
| Dicalcium phosphate | 3 |
| Immuglobuline-lysozyme | 0.5 |
| Acesulfame | 0.3 |
| Aspartame | 0.3 |
| Flavour | 2.6 |
| Green tea extract | 2 |
| *Aronia* | 0.5 |
| Xylitol | 11 |

Chewing gum piece 2 (fresh breath)
Formulation example 5

| Ingredients | % by weight |
|---|---|
| Gum base | 45 |
| Sorbitol | 36.57 |
| Maltitol syrup | 5 |
| Lecithine | 0.2 |
| *Eucaluptus* | 1.5 |
| Zinc benzoate | 0.8 |
| Acesulfame | 0.3 |
| Aspartame | 0.3 |
| Flavour | 2.6 |
| Green te extract | 4 |
| Thymol | 0.8 |
| Xylitol | 3.97 |
| *Aronia* | 1 |

Chewing gum piece 2 (gingivitis)
Formulation example 6

| Ingredients | % by weight |
|---|---|
| Gum base | 45 |
| Sorbitol | 41.17 |
| Maltitol syrup | 5 |
| Acesulfame | 0.3 |
| Aspartame | 0.3 |
| Flavour | 3.9 |
| Lecithine | 0.2 |
| Sodium fluoride | 0.03 |
| Immuglobuline-lysozyme | 2.3 |
| Osteopontin | 1.8 |

Chewing gum piece 2 (calculus)
Formulation example 7

| Ingredients | % by weight |
|---|---|
| Gum base | 45 |
| Sorbitol | 40.69 |
| Maltitol syrup | 5 |
| Lecithine | 0.2 |
| *Eucaluptus* | 1.5 |
| Sodium fluoride | 0.31 |
| Vitamin C | 4.2 |
| Citric acid | 0.5 |
| Acesulfame | 0.2 |
| Aspartame | 0.2 |
| Flavour | 2.2 |

The contents of any specific active agent or any specific composition of active agents having a specific effect, such as anti-gingivitis, can be varied according to needs. If a stronger anti-gingivitis effect is desired, the amounts of active anti-gingivitis agents are increased and vice versa. And the same applies for the other active agents, such as anti-calculus agents.

The various embodiments mentioned in the above description are non-limiting examples of the present invention. Other examples can be based by combination of the various figures, features and agents within the scope of the following claims.

The invention claimed is:

1. A tooth cleaning kit comprising at least one set of chewing gum pieces, wherein:
   i) each chewing gum piece comprises a compressed chewing gum tablet;
   ii) each compressed chewing gum tablet comprises a gum base and at least one active agent;
   iii) each compressed chewing gum tablet is formed from a compressed mixture of granules and agents;
   v) at least one first chewing gum piece comprises a different formulation than at least one second chewing gum piece;
   vi) at least one of said first and second formulations comprises an anti-gingivitis agent; and
   vii) when said tablets are chewed for at least 5 to 20 minutes, their efficacy is at least about 67 percent of that which would be obtained by brushing with a toothbrush for 2 minutes.

2. A tooth cleaning kit according to claim 1, wherein several individual sets of chewing gum pieces are included in the kit.

3. A tooth cleaning kit according to claim 2, wherein each individual set is provided for one tooth cleaning procedure.

4. A tooth cleaning kit according to claim 2, wherein the kit comprises several individual sets for use during a single day.

5. A tooth cleaning kit according to claim 2, wherein the individual set comprises several first chewing gum pieces.

6. A tooth cleaning kit according to claim 2, wherein the number of said first chewing gum pieces in the kit is higher than the number of said second chewing gum pieces.

7. A tooth cleaning kit according to claim 2, wherein the kit comprises a plurality of sets of chewing gum pieces, which sets are arranged in correspondence with a predetermined period of time, said period of time being selected from one day, one week, or one month.

8. A tooth cleaning kit according to claim 2, wherein said at least one first chewing gum piece additionally includes at least one whitening agent, at least one fresh-breath agent, at least one anti-plaque agent, or at least one re-mineralization agent.

9. A tooth cleaning kit according to claim 2, wherein said at least one first chewing gum piece additionally includes at least one anti-calculus agent.

10. A tooth cleaning kit according to claim 2, wherein said at least one second chewing gum piece additionally includes at least one whitening agent.

11. A tooth cleaning kit according to claim 2, wherein said at least one second chewing gum piece additionally includes at least one anti-plaque agent.

12. A tooth cleaning kit according to claim 2, wherein said at least one second chewing gum piece additionally includes at least one re-mineralization agent.

13. A tooth cleaning kit according to claim 2, wherein said at least one second chewing gum piece additionally includes at least one anti-calculus agent.

14. A tooth cleaning kit according to claim 1, wherein there are two or more second chewing gum pieces included in the set.

* * * * *